United States Patent
Endo et al.

(10) Patent No.: US 9,017,269 B2
(45) Date of Patent: Apr. 28, 2015

(54) BIOACOUSTIC PROCESSING APPARATUS AND BIOACOUSTIC PROCESSING METHOD

(75) Inventors: Mitsuru Endo, Tokyo (JP); Noriaki Horii, Kyoto (JP); Maki Yamada, Kanagawa (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 77 days.

(21) Appl. No.: 13/819,782

(22) PCT Filed: Mar. 9, 2012

(86) PCT No.: PCT/JP2012/001642
§ 371 (c)(1),
(2), (4) Date: Feb. 28, 2013

(87) PCT Pub. No.: WO2012/132265
PCT Pub. Date: Oct. 4, 2012

(65) Prior Publication Data
US 2013/0158435 A1  Jun. 20, 2013

(30) Foreign Application Priority Data

Mar. 25, 2011 (JP) .................................. 2011-067215
Mar. 25, 2011 (JP) .................................. 2011-067216

(51) Int. Cl.
*A61B 7/00* (2006.01)
*A61B 7/04* (2006.01)
*A61B 5/00* (2006.01)

(52) U.S. Cl.
CPC . *A61B 7/003* (2013.01); *A61B 7/04* (2013.01); *A61B 5/7203* (2013.01); *A61B 5/7264* (2013.01)

(58) Field of Classification Search
CPC ...................................... A61B 5/7203–5/7217
USPC ........................................................ 600/586
See application file for complete search history.

(56) References Cited

U.S. PATENT DOCUMENTS 5,010,889 A  4/1991  Bredesen et al.
5,213,108 A  5/1993  Bredesen et al.
(Continued)

FOREIGN PATENT DOCUMENTS

JP    3-503962 A    9/1991
JP    3035983 U    1/1997
(Continued)

OTHER PUBLICATIONS

Extended European Search Report issued in corresponding Application No. EP12765502 dated Jul. 8, 2014.
(Continued)

*Primary Examiner* — Brian Szmal
*Assistant Examiner* — H. Q. Nguyen
(74) *Attorney, Agent, or Firm* — Pearne & Gordon LLP

(57) ABSTRACT

A bioacoustic processing apparatus capable of outputting information that represents the current state of attachment of a bioacoustic sensor. The bioacoustic processing apparatus (300), which processes acoustic signals from a bioacoustic sensor (200) attached to a body surface, comprises: a noise-extracting unit (320) for extracting the noise component contained in an acoustic signal from the acoustic signal, and a noise type classification unit (340) for classifying the extracted noise component into one of a plurality of noise types that correspond to different respective states of attachment of the bioacoustic sensor (200) and outputting information that corresponds to the results of said classification.

9 Claims, 11 Drawing Sheets

(56) References Cited

U.S. PATENT DOCUMENTS

| | | |
|---|---|---|
| 5,218,969 A | 6/1993 | Bredesen et al. |
| 6,735,466 B1 | 5/2004 | Haghighi-Mood |
| 2004/0032957 A1 | 2/2004 | Mansy et al. |
| 2007/0173734 A1* | 7/2007 | Kim et al. .................. 600/546 |

FOREIGN PATENT DOCUMENTS

| | | |
|---|---|---|
| JP | 10-024033 A | 1/1998 |
| JP | 2003-510122 A | 3/2003 |
| JP | 2008-302052 A | 12/2008 |
| JP | 2009-261518 A | 11/2009 |
| JP | 2009-261723 A | 11/2009 |
| WO | 89/06932 A1 | 8/1989 |
| WO | 01/22878 A1 | 4/2001 |
| WO | 2006/067217 A2 | 6/2006 |
| WO | 2008/000254 A1 | 1/2008 |
| WO | 2008/028484 A1 | 3/2008 |

OTHER PUBLICATIONS

International Search Report for PCT/JP2012/001642 dated Apr. 17, 2012.

\* cited by examiner

FIG. 5

| NOISE TYPE | FRICTIONAL NOISE | PULSED NOISE NOT COORDINATED WITH BREATHING | PULSED NOISE COORDINATED WITH BREATHING |
|---|---|---|---|
| LEAD WIRE STATE | SOMETHING IS IN CONTACT WITH AND RUBBING AGAINST LEAD WIRE. | SOMETHING IS IN INTERMITTENT CONTACT WITH LEAD WIRE. | TENSION IN LEAD WIRE IS HIGH |
| ADHESIVE SURFACE STATE | N/A | AIR BUBBLES ARE TRAPPED BETWEEN SENSOR AND DOUBLE-SIDED TAPE (UPPER SIDE). | ADHESIVE STRENGTH BETWEEN ADHESIVE TAPE (LOWER SIDE) AND BODY SURFACE IS WEAK. |
| NOISE COUNTERMEASURE | "PLEASE MAKE SURE THAT NOTHING IS RUBBING AGAINST THE LEAD WIRE." | "PLEASE REPLACE THE DOUBLE-SIDED TAPE, MAKING SURE NO AIR BUBBLES ARE TRAPPED BETWEEN THE SENSOR AND THE TAPE. ALSO, PLEASE MAKE SURE THAT NOTHING IS IN CONTACT WITH THE LEAD WIRE." | "PLEASE REPLACE THE DOUBLE-SIDED TAPE AND PRESS FIRMLY. ALSO, PLEASE MAKE SURE THAT THE TENSION IN THE LEAD WIRE IS NOT HIGH." |

610

611, 612, 613, 614

BIOACOUSTIC PROCESSING APPARATUS AND BIOACOUSTIC PROCESSING METHOD

TECHNICAL FIELD

The claimed invention relates to a bioacoustic processing apparatus and bioacoustic processing method that process acoustic signals of an adhesive-type bioacoustic sensor.

BACKGROUND ART

Bioacoustic sensors that pick up bioacoustic signals of body sounds (e.g., heart sounds, and/or the like) are used widely. Bioacoustic processing apparatuses that process acoustic signals of bioacoustic sensors (hereinafter referred to simply as "acoustic signals"), such as when analytically processing body sounds, and/or the like, have been known.

However, acoustic signals may become contaminated with various noise components. When contaminated with noise components, analytical accuracy with respect to body sounds drops.

In view of the above, Patent Literature 1, for example, discloses a technique that reduces noise components that occur just as contact is made with a body surface, such as skin, and/or the like. With the technique disclosed in Patent Literature 1, a switch is provided on the surface of a bioacoustic sensor that contacts a body surface, and acoustic signals are muted just as the contact surface makes contact with the body surface.

Furthermore, Patent Literature 2, for example, discloses a technique that detects as noise components any sound component other than human breathing sounds. The technique disclosed in Patent Literature 2 compares acoustic signals between the immediately preceding breathing cycle and the breathing cycle that follows to determine an interval containing noise components resulting from coughing, sniffling, and/or the like, and excludes the data of that interval from the analysis.

The related art above are capable of mitigating drops in analytical accuracy for body sounds resulting from contamination by noise components.

CITATION LIST

Patent Literature

PTL 1
Japanese Patent Application Laid-Open No. HEI 10-24033
PTL 2
Japanese Patent Application Laid-Open No. 2009-261518

SUMMARY OF INVENTION

Technical Problem

With regard to modern bioacoustic sensors, ones that are used by being stuck on body surfaces by means of double-sided surgical tape, and/or the like, in order to analyze continuous body sounds over extended periods of time, for example, are popular. With such an adhesive-type bioacoustic sensor, what becomes problematic are noise components that stem from various attachment states of the bioacoustic sensor, e.g., poor adhesion with the body surface, faulty attachments of lead wires that carry acoustic signals, and so forth.

However, with the techniques disclosed in Patent Literature 1 and Patent Literature 2 mentioned above, there is a problem in that drops in analytical accuracy for body sounds resulting from the attachment state of a bioacoustic sensor cannot be mitigated sufficiently. This is because even though such noise components occur continuously after the bioacoustic sensor has been attached to a body surface, neither of the techniques disclosed in Patent Literature 1 and Patent Literature 2 is capable of detecting of such continuous noise components.

In view of the above, one may contemplate outputting information indicating the current attachment state of the bioacoustic sensor. This is because outputting such information would make it possible to mitigate drops in analytical accuracy for body sounds resulting from the attachment state of the bioacoustic sensor.

An object of the claimed invention is to provide a bioacoustic processing apparatus and bioacoustic processing method that are capable of outputting information indicating the current attachment state of a bioacoustic sensor.

Solution to Problem

A bioacoustic processing apparatus of the claimed invention includes a bioacoustic processing apparatus that processes an acoustic signal of a bioacoustic sensor attached to a body surface, the bioacoustic processing apparatus including: a noise extraction section that extracts, from the acoustic signal, a noise component included in the acoustic signal; and a noise type classification section that classifies the extracted noise component according to a plurality of noise types respectively corresponding to different attachment states of the bioacoustic sensor, and that outputs information corresponding to a result of the classification.

A bioacoustic processing method of the claimed invention includes a bioacoustic processing method that processes an acoustic signal of a bioacoustic sensor attached to a body surface, the bioacoustic processing method including the steps of: extracting, from the acoustic signal, a noise component included in the acoustic signal; and classifying the extracted noise component according to a plurality of noise types respectively corresponding to different attachment states of the bioacoustic sensor, and outputting information corresponding to a result of the classification.

Advantageous Effects of Invention

With the claimed invention, it is possible to output information indicating the current bioacoustic sensor attachment state of a bioacoustic sensor.

BRIEF DESCRIPTION OF DRAWINGS

FIG. 5 is a diagram showing example contents of a noise type-countermeasure correspondence table with respect to Embodiment 2;

DESCRIPTION OF EMBODIMENTS

Embodiments of the claimed invention are described in detail below with reference to the drawings. Embodiment 1 of the claimed invention is an example of a basic arrangement of the claimed invention. Embodiment 2 of the claimed invention is an example of a specific arrangement of the claimed invention.

Embodiment 1

Figure 1:
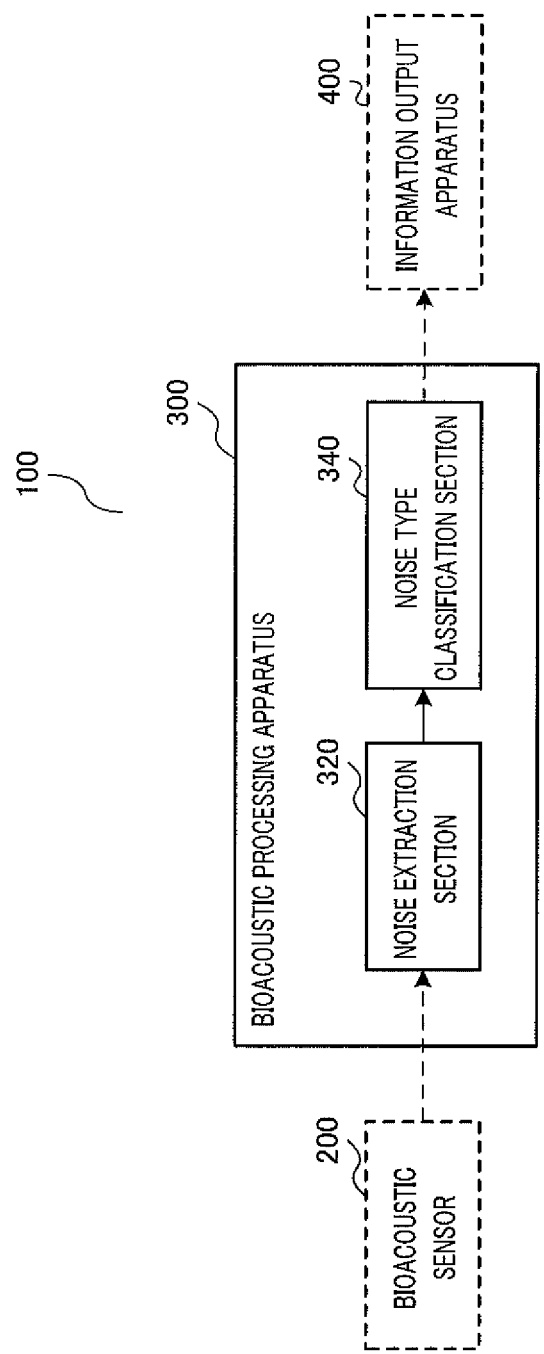
FIG. 1 is a system configuration diagram showing a configuration of a bioacoustic processing apparatus according to Embodiment 1 of the claimed invention.

FIG. 1 is a system configuration diagram showing the configuration of a bioacoustic processing apparatus according to Embodiment 1 of the claimed invention. In order to better illustrate the invention, FIG. 1 also shows a configuration of a bioacoustic processing system in which a bioacoustic processing apparatus according to the present embodiment is used.

With respect to FIG. 1, bioacoustic processing system 100 includes bioacoustic sensor 200, bioacoustic processing apparatus 300 according to the claimed invention, and information output apparatus 400.

Bioacoustic sensor 200 is a sensor to be attached to the surface of a subject's body. More specifically, bioacoustic sensor 200 may be, for example, an adhesive-type bioacoustic sensor that is used by being stuck on a body surface by means of double-sided surgical tape (hereinafter referred to simply as "double-sided tape"), and/or the like. Bioacoustic sensor 200 detects a sound that is propagated to the body surface from within the body either directly as vibration of the body surface, or indirectly as vibration of the air proximate to the body surface. Bioacoustic sensor 200 detects such vibrations (hereinafter referred to generally as "sound"), and outputs an acoustic signal indicating the waveform of the detected sound.

However, as mentioned above, an acoustic signal outputted from this bioacoustic sensor 200 (hereinafter referred to simply as "acoustic signal") may be contaminated with noise components stemming from the attachment state of bioacoustic sensor 200, e.g., poor adhesion to the skin, and/or the like.

Bioacoustic processing apparatus 300 is an apparatus that processes the above-mentioned acoustic signal. Bioacoustic processing apparatus 300 includes noise extraction section 320 and noise type classification section 340. Noise extraction section 320 extracts, from the acoustic signal, noise components included in the acoustic signal. Noise type classification section 340 classifies the extracted noise components into a plurality of noise types respectively corresponding to different attachment states of bioacoustic sensor 200, and outputs information that corresponds to the results of that classification.

By way of example, noise type classification section 340 classifies the extracted noise components into noise types corresponding to a state where the adhesive strength of the adhesive surface has become weakened, attachment states of a lead wire, and/or the like. By way of example, a noise type corresponding to a state where the adhesive strength of the adhesive surface has become weakened is a type of noise component that is caused by the weakening of the adhesive strength of the adhesive surface.

Information output apparatus 400 outputs information corresponding to the classification results of bioacoustic processing apparatus 300. By way of example, information output apparatus 400 displays on a screen information to the effect that bioacoustic sensor 200 is in a state where the adhesive strength of the adhesive surface has become weakened. Upon viewing this information, the user may replace the old double-sided tape of bioacoustic sensor 200 with new tape, or wipe the body surface, for example. As a result, the degree of adhesion of bioacoustic sensor 200 to the body surface increases, thus reducing noise components.

Bioacoustic processing apparatus 300 may include, for example: a central processing unit (CPU); a storage medium (e.g., read only memory (ROM)) storing a control program; and working memory (e.g., random access memory (RAM)). In this case, the functions of the various sections mentioned above are realized by having the CPU execute the control program.

Such a bioacoustic processing apparatus 300 is able to map noise components included in acoustic signals to attachment states of bioacoustic sensor 200. Thus, bioacoustic processing apparatus 300 is able to output information indicating the current attachment state of bioacoustic sensor 200. Accordingly, bioacoustic processing apparatus 300 is able to, for example, prompt the user to improve the attachment state of bioacoustic sensor 200. Thus, bioacoustic processing apparatus 300 is able to mitigate drops in analytical accuracy for body sounds caused by noise components stemming from the attachment state of bioacoustic sensor 200.

Thus, a bioacoustic processing apparatus of the present embodiment may be a bioacoustic processing apparatus that processes an acoustic signal of a bioacoustic sensor attached to a body surface. A bioacoustic processing apparatus of the present embodiment may include a noise extraction section that extracts, from the acoustic signal, noise components included in the acoustic signal. A bioacoustic processing apparatus of the present embodiment may include a noise type classification section that classifies the extracted noise components into a plurality of noise types respectively corresponding to different types of attachment states of the bioacoustic sensor, and that outputs information corresponding to the results of the classification.

Such a bioacoustic processing apparatus is able to output information indicating the current attachment state of the bioacoustic sensor, and to mitigate drops in analytical accuracy for body sounds caused by noise components stemming from the attachment state of the bioacoustic sensor.

Embodiment 2

Embodiment 2 of the claimed invention is an example where the claimed invention is applied to a bioacoustic processing apparatus that measures a human's heart sound or breathing sound (lung sound) as a body sound.

Figure 2:
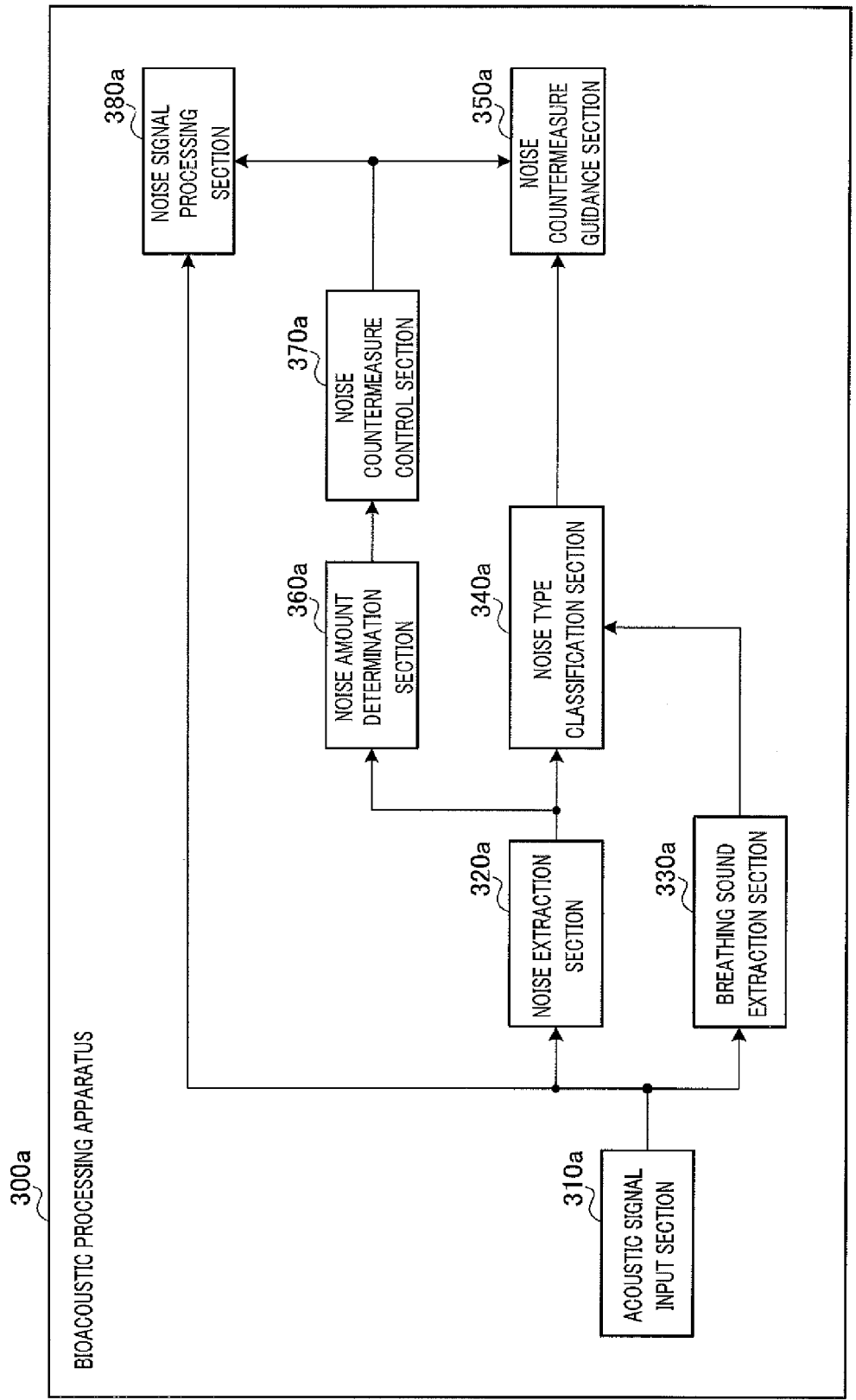
FIG. 2 is a block diagram showing an example configuration of a bioacoustic processing apparatus according to Embodiment 2 of the claimed invention.

FIG. 2 is a block diagram showing an example configuration of a bioacoustic processing apparatus according to the present embodiment. A bioacoustic processing apparatus according to the present embodiment may be used in a bioacoustic processing system similar to that in FIG. 1 of Embodiment 1.

With respect to FIG. 2, bioacoustic processing apparatus 300a includes acoustic signal input section 310a, noise extraction section 320a, breathing sound extraction section 330a, noise type classification section 340a, noise countermeasure guidance section 350a, noise amount determination section 360a, noise countermeasure control section 370a, and noise signal processing section 380a.

Acoustic signal input section 310a receives an acoustic signal of a bioacoustic sensor, and outputs it to noise extraction section 320a, breathing sound extraction section 330a, and noise signal processing section 380a. As previously discussed, this acoustic signal may be contaminated with noise components stemming from the attachment state of the bioacoustic sensor, e.g., poor adhesion to the skin, and/or the like.

Figure 3:
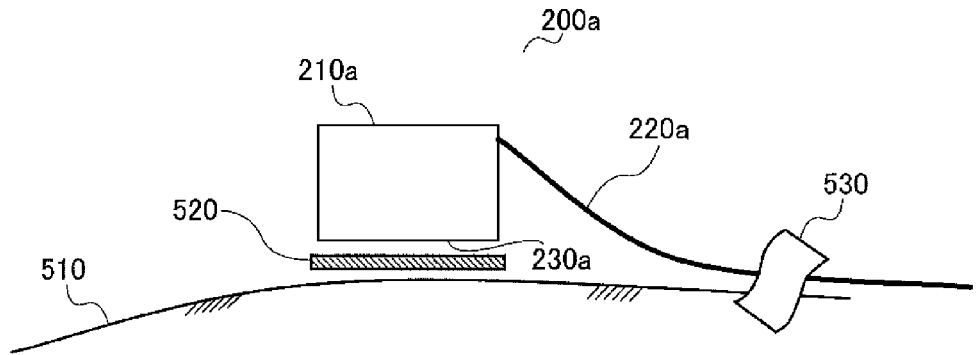
FIG. 3 is a schematic diagram showing an example attachment state of a bioacoustic sensor with respect to Embodiment 2.

FIG. 3 is a schematic diagram showing an example attachment state of a bioacoustic sensor.

As shown in FIG. 3, bioacoustic sensor 200a includes main body section 210a, which is to be attached to human body surface 510, and lead wire 220a, which is connected to main body section 210a.

Surface 230a of main body section 210a (hereinafter referred to as "adhesive surface") that is to be stuck on body surface 510 is stuck on body surface 510 by means of double-sided tape 520, for example. Specifically, when bioacoustic sensor 200a is in use, adhesive surface 230a and the upper side of double-sided tape 520 tightly adhere to each other, as do the lower side of double-sided tape 520 and body surface 510 to each other. For purposes of better visibility, they are, however, shown in a separated state in the drawing.

Lead wire 220a is fixed to body surface 510 at a position near main body section 210a by means of surgical tape 530, and/or the like, for example.

Through such adhesion and fixation, bioacoustic sensor 200a is attached to body surface 510. Specifically, bioacoustic sensor 200a is attached to the skin surface of a human's chest or neck, for example.

Main body section 210a may be a sensor of the vibration sensor type or acoustic sensor type (i.e., microphone type), and detects sound with adhesive surface 230a. Main body section 210a outputs an acoustic signal, which indicates the waveform of the detected sound, to lead wire 220a. A sensor of the vibration sensor type senses, directly as vibration, the vibration of the body surface with which adhesive surface 230a is in contact. A sensor of the acoustic sensor type senses, as sound via air vibration, the vibration of the body surface with which adhesive surface 230a is in contact.

A body sound is observed at body surface 510 as vibration. As adhesive surface 230a and body surface 510 vibrate together, a body sound is detected at main body section 210a, converted into an acoustic signal, and transmitted through lead wire 220a. However, noise components may contaminate the acoustic signal depending on the adhesion state of adhesive surface 230a with respect to body surface 510, the attachment state of lead wire 220a, and/or the like.

By way of example, body surface 510 contracts with the subject's breathing. On the other hand, a material that does not contract very well, e.g., a synthetic resin, and/or the like, is used for adhesive surface 230a. Accordingly, if the adhesive strength between double-sided tape 520 and body surface 510 is weak, pulsed noise components contaminate the acoustic signal of bioacoustic sensor 200a at a certain point in the contraction process of body surface 510 caused by breathing. By way of example, every time body surface 510 expands during breathing, noise components would occur in the acoustic signal.

Even if the adhesive strength between double-sided tape 520 and body surface 510 is sufficient, if the tension in lead wire 220a is high, the tension would fluctuate in sync with the breathing. Accordingly, pulsed noise components would contaminate the acoustic signal of bioacoustic sensor 200a.

If there are air bubbles between adhesive surface 230a and double-sided tape 520, or if lead wire 220a intermittently comes into contact with some other object, pulsed noise components that are out of sync with the breathing would contaminate the acoustic signal of bioacoustic sensor 200a.

Furthermore, if there is something that intermittently comes into contact with and rubs against lead wire 220a, frictional noise components would contaminate the acoustic signal of bioacoustic sensor 200a. Although frictional noise components could also occur when the bioacoustic sensor 200a is held in one's hand and pressed against body surface 510, this shall be disregarded with regard to the present embodiment which is premised on sticking bioacoustic sensor 200a on body surface 510.

Noise extraction section 320a in FIG. 2 extracts, from the acoustic signal, noise components included in the acoustic signal, and outputs to noise type classification section 340a and noise amount determination section 360a a time series signal of the power of the extracted noise components. The time series signal of the power of the noise components included in the acoustic signal will hereinafter be referred to as a "power waveform."

The frequency band of the noise components that could contaminate the acoustic signal covers a wide range. However, the upper end of the frequency band of heart sounds and breathing sounds is about 1 kHz. Accordingly, noise extraction section 320a extracts, as a power waveform of the noise components, a time series signal of power derived per predetermined short interval by picking up signals of or above 1 kHz by means of a high-pass filter (HPF), for example.

The predetermined short interval may be, for example, a 480-point interval if the sampling frequency of the original acoustic signal is 48 kHz. In this case, the sampling frequency of the power waveform of the noise components is 100 Hz.

Breathing sound extraction section 330a extracts, from the acoustic signal, breathing sound components included in the acoustic signal, and outputs to noise type classification section 340a a power waveform of the extracted breathing sound components. Of the frequency band of 1 kHz and below, which contains little noise, the lower frequencies contain heart sounds. Accordingly, breathing sound extraction section 330a extracts, as a power waveform of the breathing sound components, a time series of power derived per predetermined short interval mentioned above by picking up signals of 500 Hz and above but of 1 kHz and below by means of a band-pass filter (BPF), for example.

Noise type classification section 340a classifies the extracted noise components into a plurality of noise types respectively corresponding to different attachment states of bioacoustic sensor 200a. Noise type classification section 340a then outputs the results of the classification to noise countermeasure guidance section 350a. Details of this noise component classification and details of a configuration of noise type classification section 340a for performing this classification will be discussed hereinafter.

Noise countermeasure guidance section 350a presents to the user information prompting an improvement in the attachment state corresponding to the result of the noise component classification, and thus performs noise countermeasure guidance.

More specifically, noise countermeasure guidance section 350a determines whether or not the attachment state corresponding to the noise type of the extracted noise components is one that needs improvement. If it is determined that it needs improvement, noise countermeasure guidance section 350a outputs to an information output apparatus (see FIG. 1) information that notifies accordingly, and has it produce output by means of at least one of image and audio (hereinafter referred to as "noise countermeasure guidance").

However, noise countermeasure guidance section 350a is under the control of noise countermeasure control section 370a (discussed hereinbelow) as regards whether or not to perform noise countermeasure guidance (that is, it is subject to the above-mentioned determination as to whether or not the attachment state is one that needs improvement). Details of a method, with respect to noise countermeasure guidance section 350a, of determining the noise countermeasure to be suggested will be discussed hereinafter.

Noise amount determination section 360a quantifies, as a noise amount, the strength of the noise components in the acoustic signal based on the power waveform of the noise components, and outputs it to noise countermeasure control section 370a. More specifically, noise amount determination section 360a determines, as a noise amount, the incidence or interval ratio, over a given period, of intervals during which the power waveform of the noise components exceeds a predefined first threshold. This given period may be, for example, the length of the interval during which the power waveform of the breathing sound components exceeds a predefined second threshold.

Noise countermeasure control section 370a controls noise countermeasures based on noise amount. More specifically, if the noise amount exceeds a pre-defined third threshold, noise countermeasure control section 370a instructs noise countermeasure guidance section 350a to perform noise countermeasure guidance. On the other hand, if the noise amount does not exceed the third threshold, noise countermeasure control section 370a instructs the later-discussed signal processing-based noise countermeasure to noise signal processing section 380a.

Noise amount sometimes has a property where, after beginning measurement of body sounds, it decreases over the course of several breathing cycles. In view of this property, noise countermeasure control section 370a may defer the threshold judgment while the noise amount is showing a decreasing trend, and not perform any noise countermeasure.

If the impact of the extracted noise components is limited and there is no particular need to improve the attachment state, noise signal processing section 380a performs, on the acoustic signal, ordinary signal processing for eliminating noise components. More specifically, noise signal processing section 380a performs such signal processing as masking a region where, with respect to the frequency domain or time domain, noise components may exist, thereby reducing the impact of noise components with respect to bioacoustic measurements that are based on the acoustic signal.

However, as mentioned above, noise signal processing section 380a is under the control of noise countermeasure control section 370a as regards whether or not to perform a signal processing-based noise countermeasure (that is, it is subject to the above-mentioned determination as to whether or not the attachment state does not need improvement).

Bioacoustic processing apparatus 300a may include, for example: a CPU; a storage medium (e.g., ROM, and/or the like) storing a control program; and working memory (e.g., RAM, and/or the like). In this case, the functions of the various sections mentioned above are realized by having the CPU execute the control program.

Such a bioacoustic processing apparatus 300a is able to map noise components included in acoustic signals to attachment states of bioacoustic sensor 200a. Accordingly, bioacoustic processing apparatus 300a is able to prompt the user to improve the attachment state of bioacoustic sensor 200a in accordance with noise type. Thus, bioacoustic processing apparatus 300a is able to mitigate drops in analytical accuracy for body sounds stemming from the attachment state of bioacoustic sensor 200a.

When there is no need to improve the attachment state, bioacoustic processing apparatus 300a performs signal processing for eliminating noise components. Accordingly, bioacoustic processing apparatus 300a is able to reduce the frequency of reattachments, while at the same time mitigating drops in analytical accuracy for body sounds stemming from the attachment state of bioacoustic sensor 200a, thereby ameliorating the burden on the user.

Next, details of noise component classification and details of a configuration of noise type classification section 340a for performing this classification are discussed.

Figure 4:
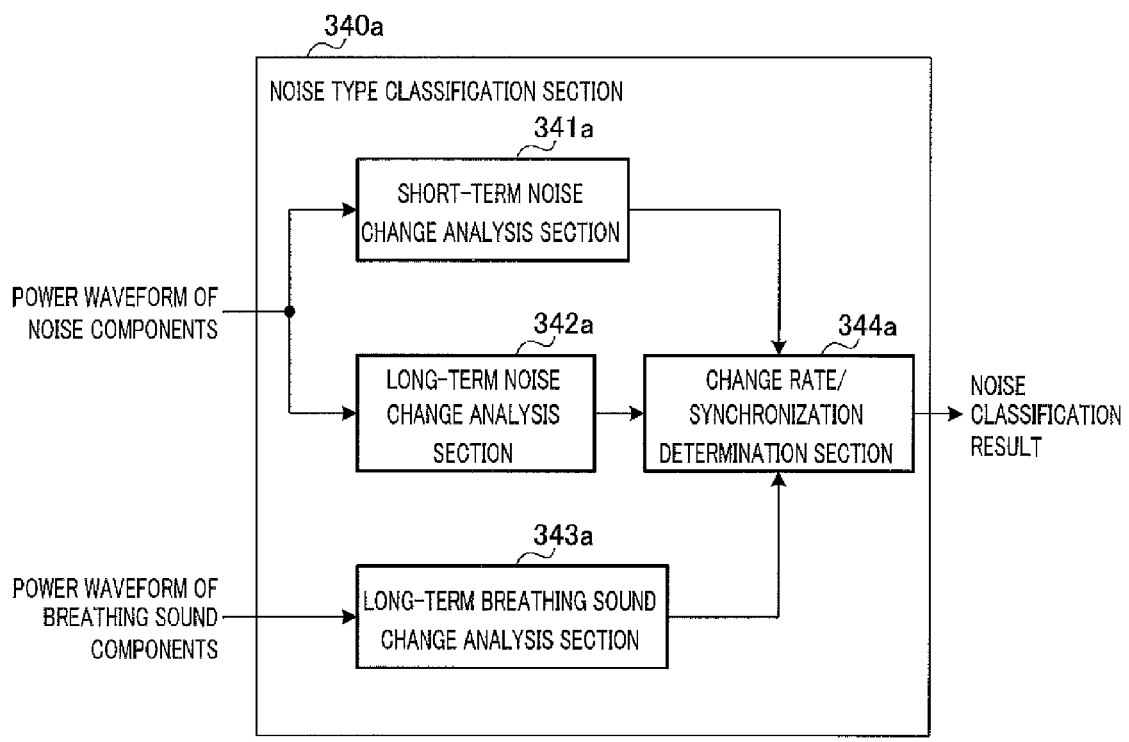
FIG. 4 is a block diagram showing an example configuration of a noise type classification section with respect to Embodiment 2.

FIG. 4 is a block diagram showing an example configuration of noise type classification section 340a.

With respect to FIG. 4, noise type classification section 340a includes short-term noise change analysis section 341a, long-term noise change analysis section 342a, long-term breathing sound change analysis section 343a, and change rate/synchronization determination section 344a.

Based on the power waveform of the noise components, short-term noise change analysis section 341a extracts, of the changes with periods shorter than the minimum value of a typical period for breathing (i.e., of the high-frequency components), the frequency band with the greatest power. This frequency band will hereinafter be referred to as a "short-term peak frequency band of noise components."

Short-tend noise change analysis section 341a outputs to change rate/synchronization determination section 344a the extracted short-term peak frequency band of the noise components. This extraction may be performed by processing the power waveform of the noise components with a 50-point fast Fourier transform (FFT), for example. The short-term peak frequency band of the noise components is high when the noise components of the acoustic signal are pulsed, and low when the noise components of the acoustic signal are frictional.

Based on the power waveform of the noise components, with respect to changes with periods longer than the minimum value of a typical period for breathing (i.e., low-frequency components), long-term change analysis section 342a ranks the powers of the respective frequency bands by magnitude. Long-term noise change analysis section 342a outputs to change rate/synchronization determination section 344a the power ranking of the frequency bands (hereinafter referred to as "noise power ranking") Frequency bands that rank high in the noise power ranking would include the later-discussed breathing sound peak frequency band if there is a strong relationship between the cause of the noise components and breathing.

Based on the power waveform of the breathing sound components, long-term breathing sound change analysis section 343a extracts, of the changes with periods longer than the minimum value of a typical period for breathing (i.e., low-frequency components), the frequency band with the greatest power (hereinafter referred to as a "breathing sound peak frequency band"). Long-term breathing sound change analysis section 343a outputs the extracted breathing sound peak frequency band to change rate/synchronization determination section 344a. The breathing sound peak frequency band accurately indicates the period of the breathing.

Based on the short-term peak frequency band of the noise components, change rate/synchronization determination section 344a determines whether the change in the power waveform of the noise components is fast or slow (i.e., the rate of change of the power of the noise components). Based on whether the change in the power waveform of the noise components is fast or slow, change rate/synchronization determination section 344a determines whether the noise components are pulsed or frictional.

More specifically, change rate/synchronization determination section 344a determines the noise components of the acoustic signal to be pulsed when the short-teen peak frequency band of the noise components is 10 Hz or above, for example. On the other hand, change rate/synchronization determination section 344a may determine the noise components of the acoustic signal to be frictional when the short-term peak frequency band of the noise components is less than 10 Hz.

Based on the breathing sound peak frequency band, change rate/synchronization determination section 344a determines whether or not the occurrences of noise components are in sync with breathing. More specifically, change rate/synchronization determination section 344a determines whether or not the breathing sound peak frequency band is included in the frequency bands that rank high in the noise power ranking. In other words, change rate/synchronization determination section 344a compares the change in the power waveform of the breathing sound components and the change in the power waveform of the noise components, and determines whether or not the two are coordinated.

If the occurrences of noise components are in sync with breathing, change rate/synchronization determination section 344a determines the noise components to be breathing-synchronous. On the other hand, if the occurrences of noise components are not in sync with breathing, change rate/synchronization determination section 344a determines the noise components to be breathing-asynchronous.

If it is determined that the noise components of the acoustic signal are frictional (i.e., not pulsed), change rate/synchronization determination section 344a need not necessarily assess the synchronization between the noise components and breathing. Also, in order to accurately assess the synchronization between the noise components and breathing, analysis over a time span of about two breathing cycles is necessary. Accordingly, change rate/synchronization determination section 344a may withhold synchronization assessment until analysis of this time span is completed.

Based on the above-mentioned determination result, change rate/synchronization determination section 344a classifies the noise components of the acoustic signal into a plurality of noise types respectively corresponding to different attachments states of bioacoustic sensor 200a. Change rate/synchronization determination section 344a outputs, to noise countermeasure guidance section 350a in FIG. 2, a noise classification result indicating which noise type they have been classified as.

With respect to the present embodiment, the plurality of noise types include, for example, three types, namely, "frictional noise," "pulsed noise not coordinated with breathing," and "pulsed noise coordinated with breathing."

If the noise components of the acoustic signal are frictional, change rate/synchronization determination section 344a classifies those noise components as "frictional noise."

If the noise components of the acoustic signal are pulsed and breathing-asynchronous, change rate/synchronization determination section 344a classifies those noise components as "pulsed noise not coordinated with breathing."

If the noise components of the acoustic signal are pulsed and breathing-synchronous, change rate/synchronization determination section 344a classifies those noise components as "pulsed noise coordinated with breathing."

Next, details of the mapping between noise type and attachment state, as well as details of a method, with respect to noise countermeasure guidance section 350a, of determining a noise countermeasure to be suggested are discussed.

Noise countermeasure guidance section 350a has a noise type-countermeasure correspondence table stored therein in advance. The noise type-countermeasure correspondence table includes information indicating correspondence relationships between noise types and attachment states, as well as correspondence relationships between attachment states and noise countermeasures to be suggested to the user.

Noise countermeasure guidance section 350a references this noise type-countermeasure correspondence table each time a noise classification result is received. Noise countermeasure guidance section 350a determines the noise countermeasure corresponding to the noise type indicated by the noise classification result to be the noise countermeasure to be presented (suggested) to the user.

FIG. 5 is a diagram showing example contents of a noise type-countermeasure correspondence table.

As shown in FIG. 5, noise type-countermeasure correspondence table 610 maps noise types 611 to states 612 of lead wire 220a and states 613 of adhesive surface 230a, which are attachment states of bioacoustic sensor 200a. Noise type-countermeasure correspondence table 610 maps noise types 611 (each a pair of state 612 of lead wire 220a and state 613 of adhesive surface 230a) to noise countermeasures 614.

The pairs, which are each made up of state 612 of lead wire 220a and state 613 of adhesive surface 230a, indicate attachment states of bioacoustic sensor 200a that are likely causing the corresponding noise components. Noise countermeasures 614 are each an effective means for eliminating the cause of the corresponding noise components, and are noise countermeasures to be suggested.

Noise type-countermeasure correspondence table 610 maps, for example, noise countermeasure 614 that says "please make sure that nothing is rubbing against the lead wire" to noise type 611 of "frictional noise." This is because state 612 of lead wire 220a where "something is in contact with and rubbing against the lead wire" (i.e., a first state) is likely a cause of frictional noise.

Furthermore, noise type-countermeasure correspondence table 610 maps, for example, noise countermeasure 614 that says "please replace the double-sided tape, making sure no air bubbles are trapped between the sensor and the tape. Also, please make sure that nothing is in contact with the lead wire," to noise type 611 of "pulsed noise not coordinated with breathing."

This is because state 612 of lead wire 220a where "something is in intermittent contact with the lead wire" is likely a cause of pulsed noise not coordinated with breathing.

Furthermore, this is because state 613 of adhesive surface 230a where "air bubbles are trapped between the sensor and the double-sided tape (upper side)" (i.e., a second state) is likely a cause of pulsed noise not coordinated with breathing.

Furthermore, noise type-countermeasure correspondence table 610 maps, for example, noise countermeasure 614 that says "please replace the double-sided tape and press firmly. Also, please make sure that the tension in the lead wire is not high," to noise type 611 of "pulsed noise coordinated with breathing."

This is because state 612 of lead wire 220a where "the tension in the lead wire is high" is likely a cause of pulsed noise coordinated with breathing. Similarly, this is because state 613 of adhesive surface 230a where "the adhesive strength between the double-sided tape (lower side) and the body surface is weak" (i.e., a third state) is likely a cause of pulsed noise coordinated with breathing.

Noise type-countermeasure correspondence table 610 need not necessarily include state 612 of lead wire 220a and state 613 of adhesive surface 230a.

With respect to noise countermeasures 614, noise type-countermeasure correspondence table 610 may separately include those mapped to states 612 of lead wire 220a and those mapped to states 613 of adhesive surface 230a. Alternatively, noise type-countermeasure correspondence table 610 may include just one of the two above.

Noise type-countermeasure correspondence table 610 may also include as noise countermeasures 614 means for eliminating other causes related to the attachment state of bioacoustic sensor 200a.

Furthermore, noise type-countermeasure correspondence table 610 may divide noise countermeasures 614 into a plurality of levels. In this case, bioacoustic sensor 200a would, for example, select first-level noise countermeasure 614 the first time around, and select second-level noise countermeasure 614 the second time around.

The task of re-sticking bioacoustic sensor 200a is relatively burdensome. Accordingly, noise type-countermeasure correspondence table 610 may include, as first-level noise countermeasure 614, making sure nothing is in contact with the lead wire, and, as second-level noise countermeasure 614, re-sticking bioacoustic sensor 200a.

Next, operations of bioacoustic processing apparatus 300a are described.

Figure 6:
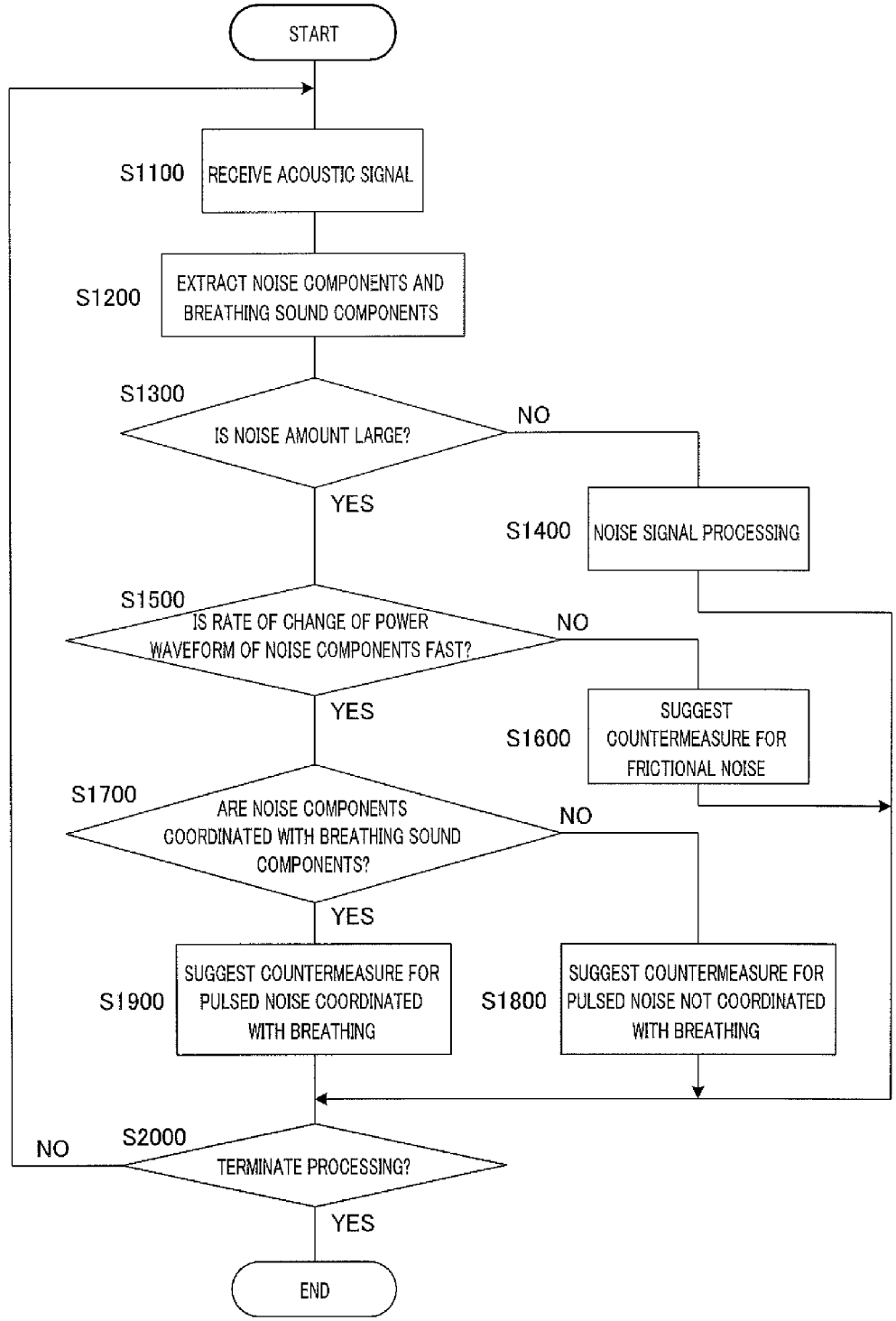
FIG. 6 is a flowchart showing an example operation of a bioacoustic processing apparatus according to Embodiment 2.

FIG. 6 is a flowchart showing example operations of a bioacoustic processing apparatus.

First, in step S1100, acoustic signal input section 310a receives an acoustic signal from bioacoustic sensor 200a.

In step S1200, noise extraction section 320a extracts noise components from the acoustic signal, and generates a power waveform of the noise components. Furthermore, breathing sound extraction section 330a extracts breathing sound components from the acoustic signal, and generates a power waveform of the breathing sound components.

In step S1300, based on the power waveform of the noise components, noise amount determination section 360a computes a noise amount, which represents the strength of the noise components with respect to the acoustic signal. Furthermore, noise countermeasure control section 370a determines whether or not the computed noise amount is large. Specifically, noise countermeasure control section 370a determines whether or not the noise amount exceeds a predetermined threshold (i.e., the above-mentioned third threshold).

If the noise amount is not large (S1300: NO), noise countermeasure control section 370a proceeds to step S1400.

In step S1400, noise countermeasure control section 370a causes noise signal processing section 380a to perform a signal processing-based noise countermeasure, and proceeds to step S2000, which is described hereinbelow.

On the other hand, if the noise amount is large (S1300: YES), noise countermeasure control section 370a proceeds to step S1500.

In step S1500, noise type classification section 340a determines whether or not the change in the power waveform of the noise components is fast.

Specifically, noise type classification section 340a identifies a short-term peak frequency band at short-term noise change analysis section 341a. Noise type classification section 340a then determines at change rate/synchronization determination section 344a whether or not the identified short-term peak frequency band is of a predetermined threshold (e.g., 10 Hz, as mentioned above) or greater.

If the change in the power waveform of the noise components is not fast (S1500: NO), noise type classification section 340a proceeds to step S1600.

In step S1600, noise countermeasure control section 370a instructs noise countermeasure guidance section 350a to suggest a noise countermeasure for frictional noise, and proceeds to step S2000, which is described hereinbelow.

Specifically, noise type classification section 340a first classifies the noise components of the acoustic signal as "frictional noise" at change rate/synchronization determination section 344a. Noise countermeasure guidance section 350a then references the noise type-countermeasure correspondence table (see FIG. 5), and determines the noise countermeasure corresponding to "frictional noise" to be the noise countermeasure that should be suggested.

Furthermore, noise countermeasure control section 370a makes noise countermeasure guidance section 350a output, to an information output apparatus (see FIG. 1), the noise countermeasure determined by noise countermeasure guidance section 350a.

On the other hand, if the change in the power waveform of the noise components is fast (S1500: YES), noise type classification section 340a proceeds to step S1700.

In step S1700, noise type classification section 340a determines whether or not the noise components are coordinated with the breathing sound components.

Specifically, noise type classification section 340a determines a noise power ranking at long-term noise change analysis section 342a. Furthermore, noise type classification section 340a extracts a breathing sound peak frequency band at long-term breathing sound change analysis section 343a. Noise type classification section 340a then determines, at change rate/synchronization determination section 344a, whether or not the breathing sound peak frequency band ranks high in the noise power ranking (e.g., among the top three).

If the noise components are not coordinated with the breathing sound components (S1700: NO), noise type classification section 340a proceeds to step S1800.

In step S1800, noise countermeasure control section 370a instructs noise countermeasure guidance section 350a to suggest a noise countermeasure for pulsed noise not coordinated with breathing, and proceeds to step S2000, which is described hereinbelow.

Specifically, noise type classification section 340a first classifies the noise components of the acoustic signal as "pulsed noise not coordinated with breathing" at change rate/synchronization determination section 344a. Noise countermeasure guidance section 350a then references the noise type-countermeasure correspondence table (see FIG. 5), and determines the noise countermeasure corresponding to "pulsed noise not coordinated with breathing" to be the noise countermeasure that should be suggested.

Furthermore, noise countermeasure control section 370a makes noise countermeasure guidance section 350a output, to the information output apparatus (see FIG. 1), the noise countermeasure determined by noise countermeasure guidance section 350a.

On the other hand, if the noise components are coordinated with the breathing sound components (S1700: YES), noise type classification section 340a proceeds to step S1900.

In step S1900, noise countermeasure control section 370a instructs noise countermeasure guidance section 350a to suggest a noise countermeasure for pulsed noise coordinated with breathing, and proceeds to step S2000, which is described hereinbelow.

Specifically, noise type classification section 340a first classifies the noise components of the acoustic signal as "pulsed noise coordinated with breathing" at change rate/synchronization determination section 344a. Noise countermeasure guidance section 350a then references the noise type-countermeasure correspondence table (see FIG. 5), and determines the noise countermeasure corresponding to "pulsed noise coordinated with breathing" to be the noise countermeasure that should be suggested.

Furthermore, noise countermeasure control section 370a makes noise countermeasure guidance section 350a output, to the information output apparatus (see FIG. 1), the noise countermeasure determined by noise countermeasure guidance section 350a.

By way of example, noise countermeasure guidance section 350a references the noise type-countermeasure correspondence table, obtains the text data for the noise countermeasure to be suggested, generates image data including this text data, and has it visually displayed by the information output apparatus.

Alternatively, by way of example, noise countermeasure guidance section 350a obtains or generates audio data of a reading of the noise countermeasure to be suggested, and has it audially output by the information output apparatus.

Alternatively, by way of example, noise countermeasure guidance section 350a obtains, from among image or audio data pre-defined for each noise countermeasure, the data corresponding to the noise countermeasure to be suggested, and has it output by the information output apparatus.

In step S2000, acoustic signal input section 310a determines whether or not termination of processing has been instructed through user input, and/or the like.

If termination of processing has not been instructed (S2000: NO), acoustic signal input section 310a returns to step S1100. On the other hand, if termination of processing has been instructed (S2000: YES), acoustic signal input section 310a terminates the flow of processing.

Through such operations, bioacoustic processing apparatus 300a is able to classify the noise components included in the acoustic signal into a plurality of noise types respectively corresponding to attachment states of bioacoustic sensor 200a, and to suggest to the user a noise countermeasure that suits the classification result.

The following are descriptions regarding differences in the acoustic signal caused by differences in the attachment state, as well as regarding differences in the short-term peak frequency band and the long-term breathing sound peak waveform caused by differences in the sound components.

FIG. 7 through FIG. 10 are diagrams showing examples of acoustic signal spectrograms.

Figure 7:
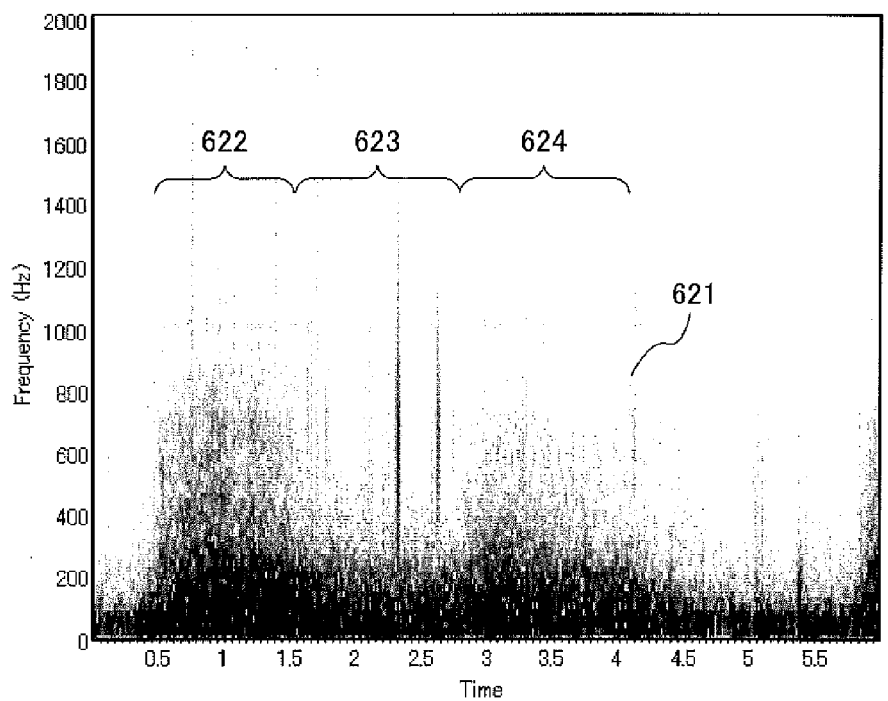
FIG. 7 is a diagram showing a spectrogram example of an acoustic signal for a case of a favorable attachment state with respect to Embodiment 2.
Figure 8:
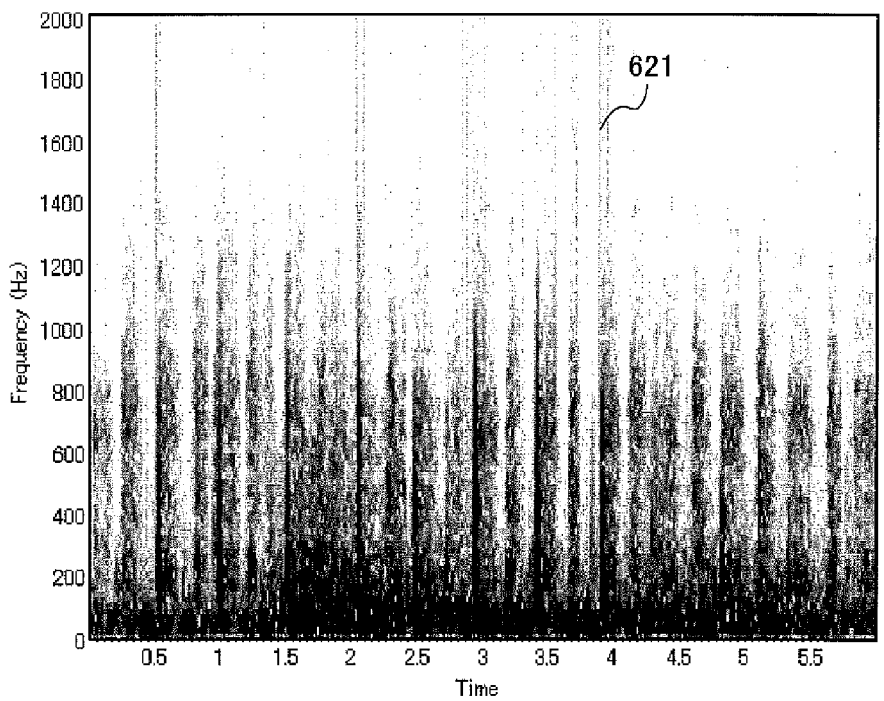
FIG. 8 is a diagram showing a first example of a spectrogram of an acoustic signal for a case of a poor attachment state with respect to Embodiment 2.
Figure 9:
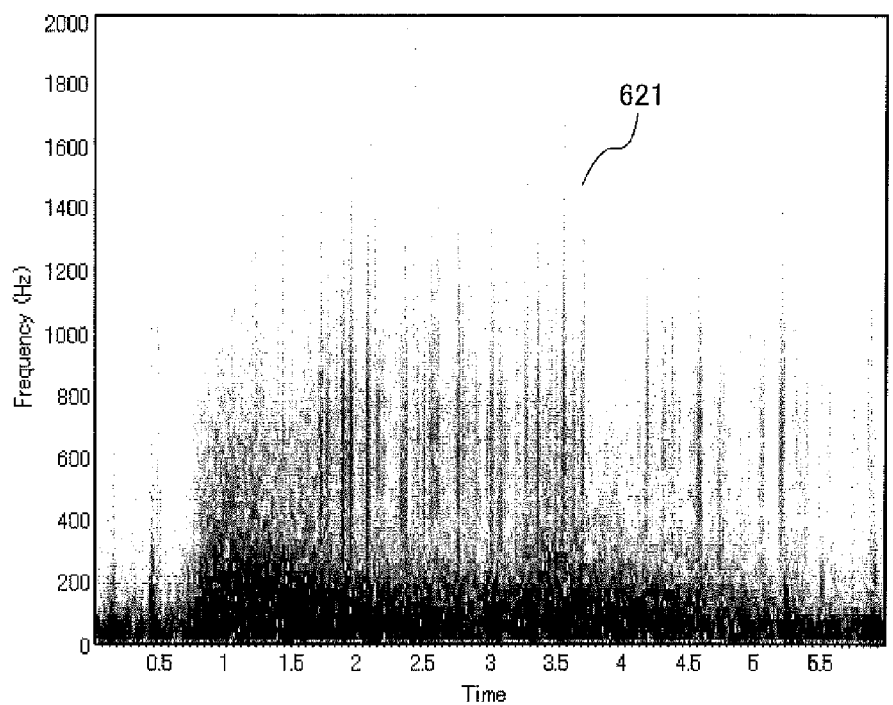
FIG. 9 is a diagram showing a second example of a spectrogram of an acoustic signal for a case of a poor attachment state with respect to Embodiment 2.
Figure 10:
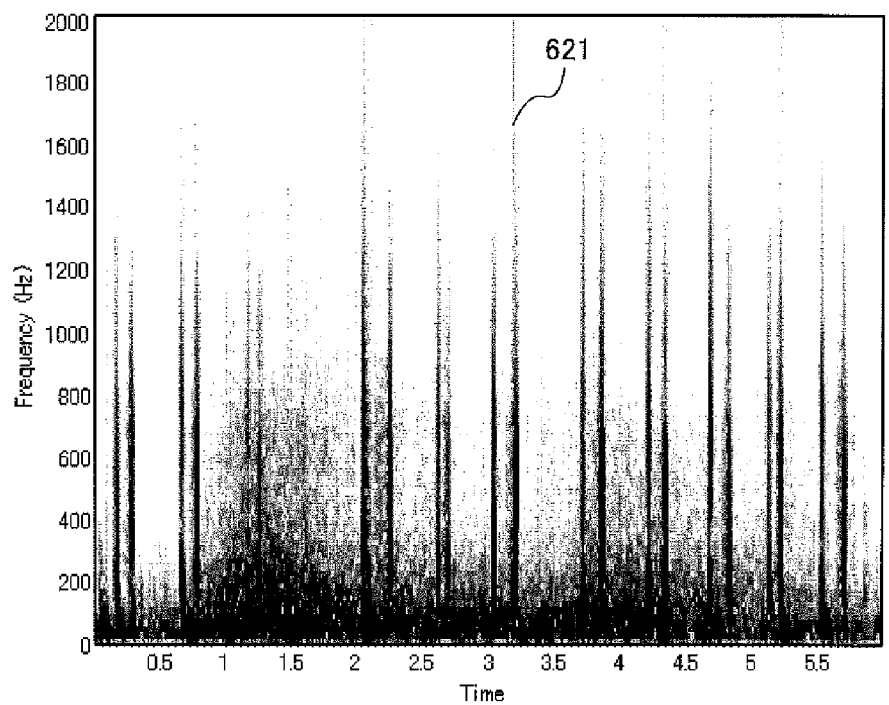
FIG. 10 is a diagram showing a third example of a spectrogram of an acoustic signal for a case of a poor attachment state with respect to Embodiment 2.

Specifically, FIG. 7 through FIG. 10 show spectrogram experiment data for the acoustic signal of bioacoustic sensor 200a placed in the second intercostal space along the right midclavicular line of the same subject. However, FIG. 7 shows data for a case where the attachment state of bioacoustic sensor 200a is favorable. FIG. 8 through FIG. 10 show data for cases where the attachment state of bioacoustic sensor 200a is poor.

When the attachment state of bioacoustic sensor 200a is favorable, noise components 621 are limited, as shown in FIG. 7, and it is easy to observe inhalation interval 622, pause interval 623, and exhalation interval 624. Accordingly, it is possible to perform breathing sound analysis, such as estimating the condition of an asthma patient's airway, and so forth, accurately through a signal processing-based noise countermeasure.

However, when the attachment state of bioacoustic sensor 200a is poor, noise components 621 increase, as shown in FIG. 8 through FIG. 10, and it becomes difficult to observe the various intervals mentioned above. In this case, it would be difficult to perform breathing sound analysis accurately even if one performed signal-processing based noise countermeasures.

FIG. 11 through FIG. 18 are diagrams showing differences in the short-term peak frequency band and the long-term breathing sound peak waveform caused by differences in the sound components.

Figure 11:
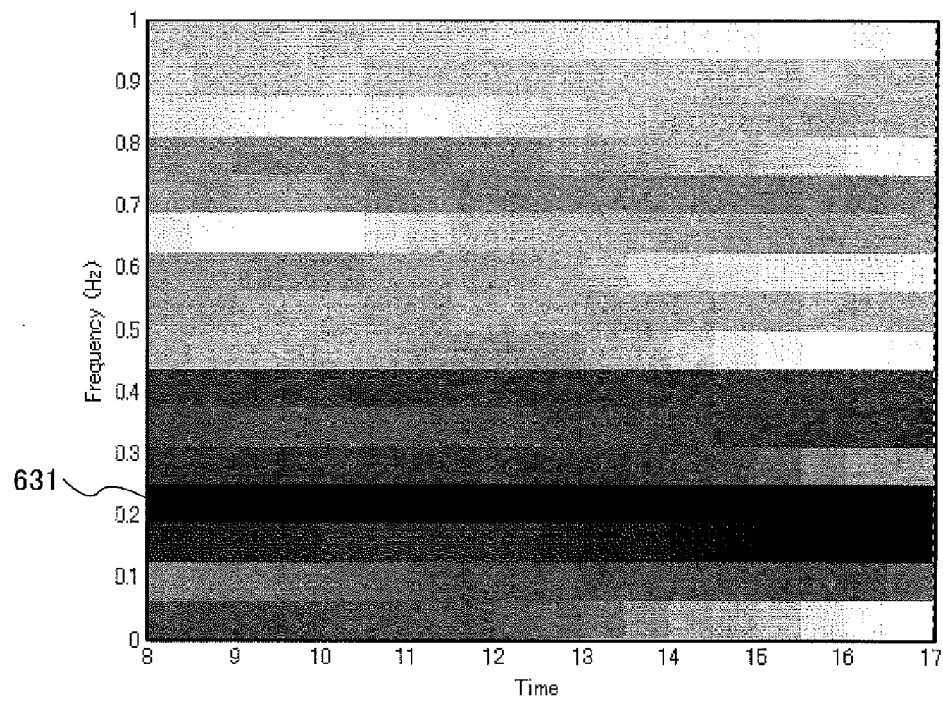
FIG. 11 is a first diagram indicating the power of the frequency band of breathing sound components for a case of pulsed noise that is coordinated with breathing with respect to Embodiment 2.

FIG. 11 is a diagram showing, through different shades of darkness, the power of each frequency band of the breathing sound components with respect to an acoustic signal that includes pulsed noise coordinated with breathing.

Specifically, FIG. 11 shows analysis results with respect to a case where a power waveform of the breathing sound components is extracted at a sampling frequency of 100 Hz from an acoustic signal obtained from a subject whose breathing cycle lasts approximately 5 seconds. FIG. 11 shows, as a spectrogram, the results obtained by down-sampling the extracted power waveform of the breathing sound components at a sampling frequency of 2 Hz, and by processing it with a 32-point (equivalent to 16 seconds) FFT.

Figure 12:
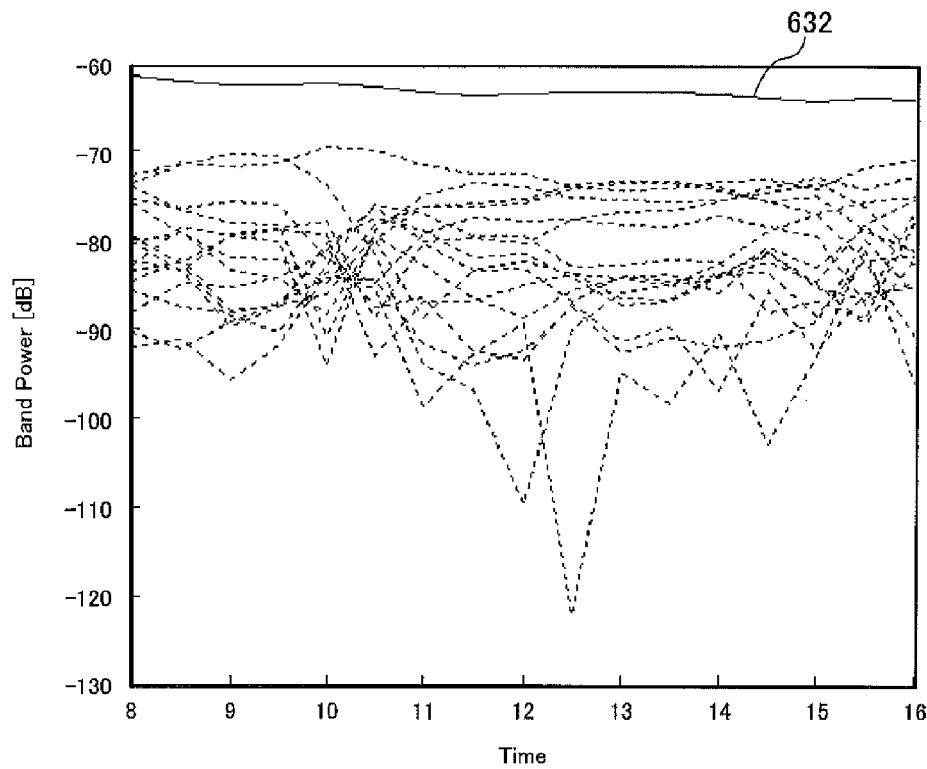
FIG. 12 is a second diagram indicating a state of breathing sound components for a case of pulsed noise that is coordinated with breathing with respect to Embodiment 2.

With respect to FIG. 11, the horizontal axis represents time, and the vertical axis represents frequency band. FIG. 12 is a diagram whose vertical axis represents the power of each frequency band in FIG. 11.

As shown in FIG. 11, with the power waveform of the breathing sound components, when the breathing cycle lasts approximately 5 seconds, the power is high in the vicinity of approximately 0.2 Hz, which corresponds thereto. Accordingly, in this case, the long-term peak frequency band of the breathing sound components would be frequency band 631, which is in the vicinity of approximately 0.2 Hz.

Furthermore, the power of frequency band 631 in FIG. 11 as indicated by solid line 632 in FIG. 12 would naturally rank highest with respect to the vertical axis representing the power of the frequency band.

Figure 13:
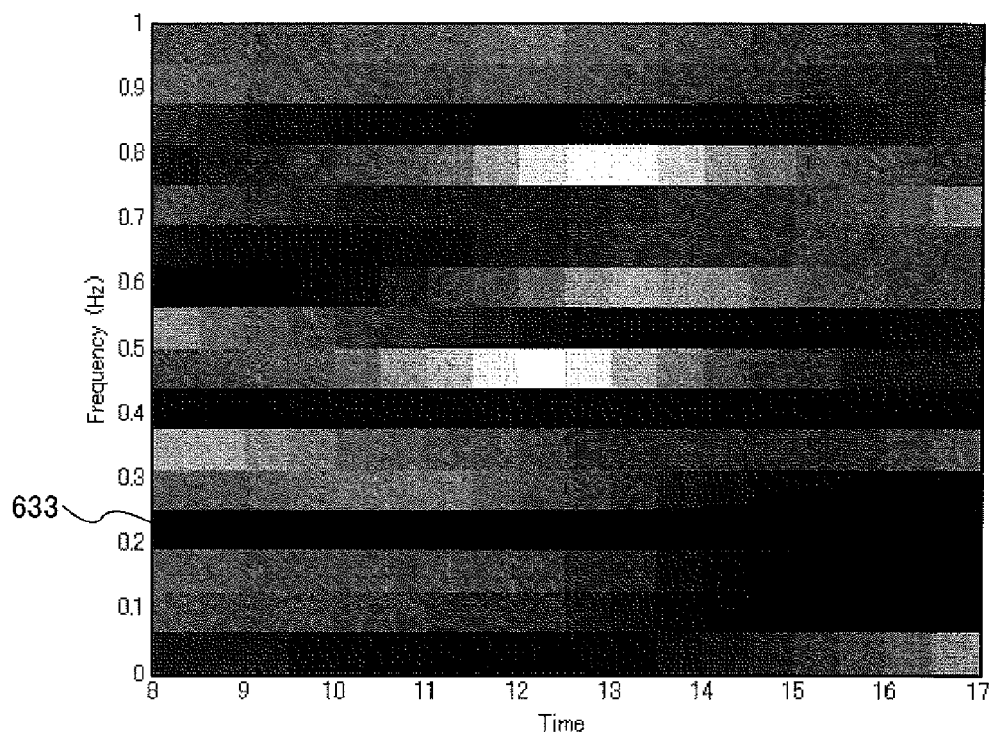
FIG. 13 is a first diagram indicating a state of noise components for a case of pulsed noise that is coordinated with breathing with respect to Embodiment 2.

FIG. 13 is a diagram showing, through different shades of darkness, the power of each frequency band of the noise components with respect to the same acoustic signal as that in FIG. 11, and is a diagram corresponding to FIG. 11. Furthermore, FIG. 14 is a diagram whose vertical axis represents the power level of each frequency band in FIG. 13, and is a diagram corresponding to FIG. 12.

Figure 14:
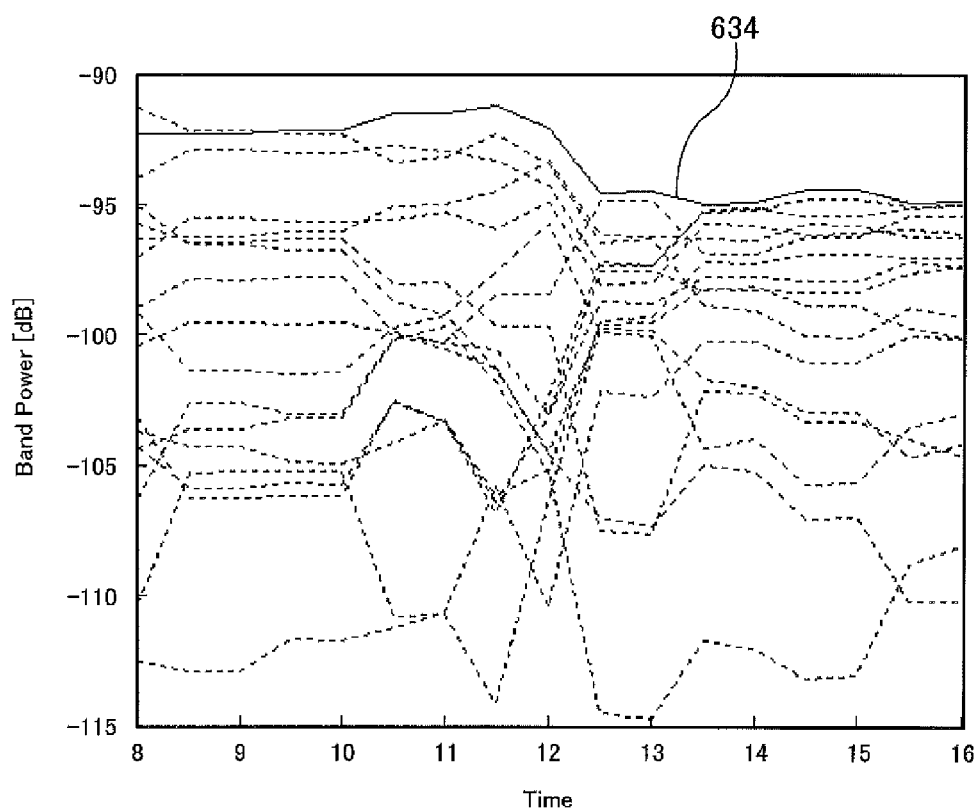
FIG. 14 is a second diagram indicating a state of noise components for a case of pulsed noise that is coordinated with breathing with respect to Embodiment 2.

Noise components corresponding to the breathing cycle, which are indicated by frequency band 633 in FIG. 13 and solid line 634 in FIG. 14, are greater than the noise components of the other frequency bands. This fact indicates that the noise is occurring in coordination with breathing.

With respect to the present experiment, long-term noise change analysis section 342*a* applies an HPF to the power waveform of the noise components with a cut-off frequency of 25 Hz. This is to extract noise components with relatively fast rates of change, and to eliminate breathing sound components that remain in the power waveform of the noise components.

When no such HPF is applied, with respect to FIG. 14, the noise power rank of the breathing sound peak frequency band (in this case corresponding to solid line 634) has been observed to drop to a lower rank. This indicates that the power waveform of the noise components includes components of a pulsed waveform that occur in sync with the breathing cycle, and not components of a waveform resembling a sinusoidal wave that coincides with the breathing cycle.

Figure 15:
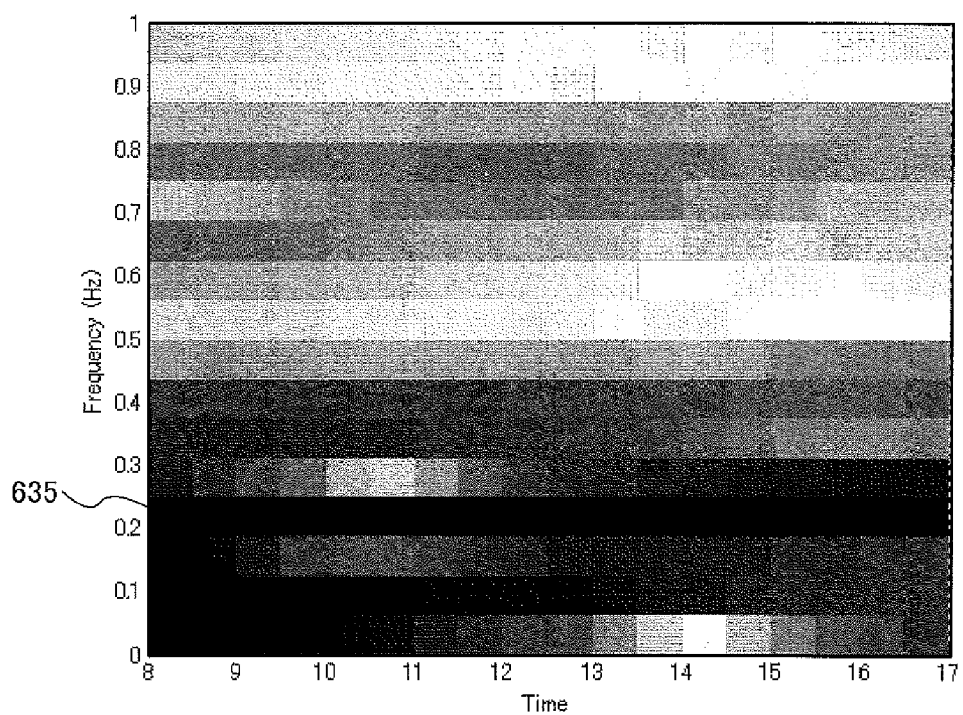
FIG. 15 is a first diagram indicating a state of breathing sound components for a case of pulsed noise that is not coordinated with breathing with respect to Embodiment 2.
Figure 16:
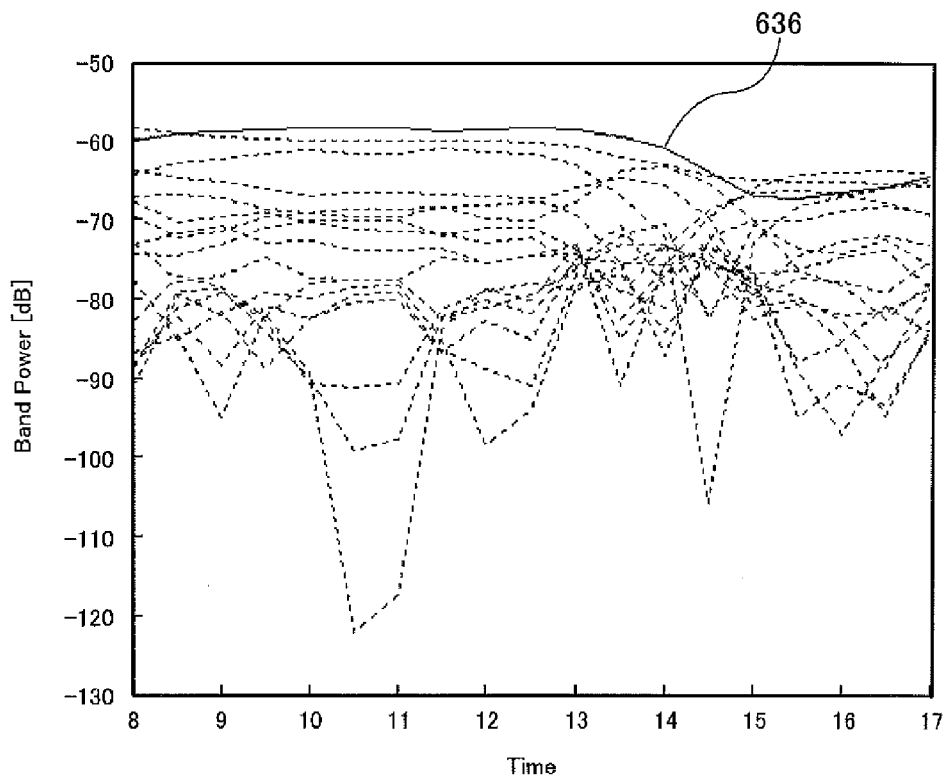
FIG. 16 is a second diagram indicating a state of breathing sound components for a case of pulsed noise that is not coordinated with breathing with respect to Embodiment 2.

FIG. 15 is a diagram showing, through different shades of darkness, the power of each frequency band of the breathing sound components with respect to an acoustic signal including pulsed noise that is not coordinated with breathing, and is a diagram corresponding to FIG. 11. Furthermore, FIG. 16 is a diagram whose vertical axis represents the power of each frequency band in FIG. 15, and is a diagram corresponding to FIG. 12.

As shown in FIG. 15, even when pulsed noise not coordinated with breathing is included, the long-term peak frequency band of the breathing sound components is frequency band 635, which is in the vicinity of approximately 0.2 Hz, which corresponds to the breathing cycle. Furthermore, the power of frequency band 635 in FIG. 15 as indicated by solid line 636 in FIG. 16 would naturally rank highest with respect to the vertical axis representing the power of the frequency band.

Figure 17:
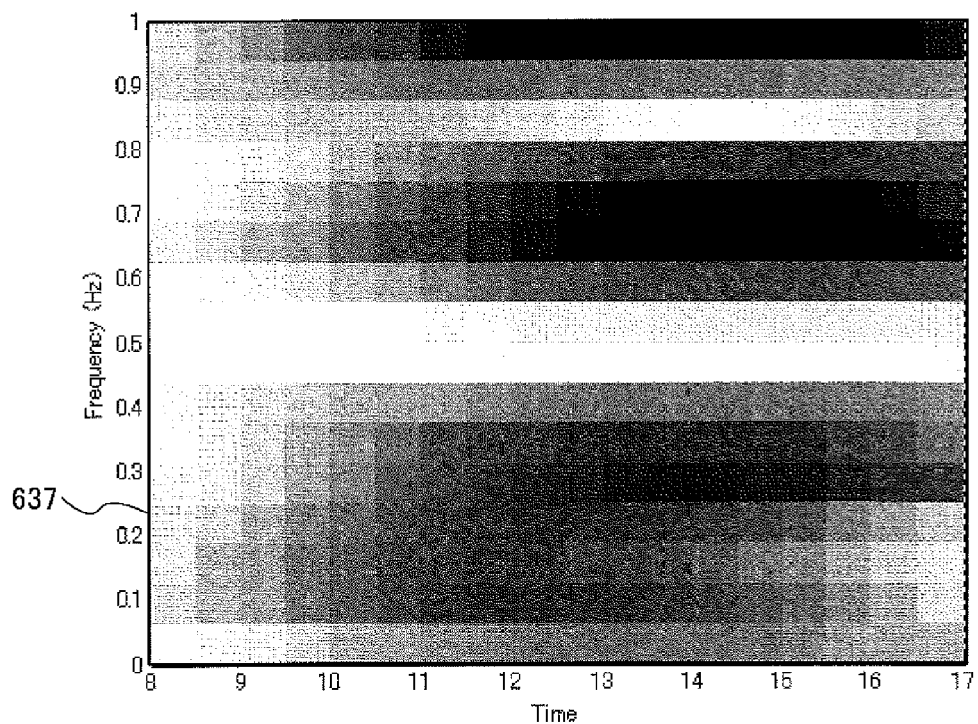
FIG. 17 is a first diagram indicating a state of noise components for a case of pulsed noise that is not coordinated with breathing with respect to Embodiment 2.
Figure 18:
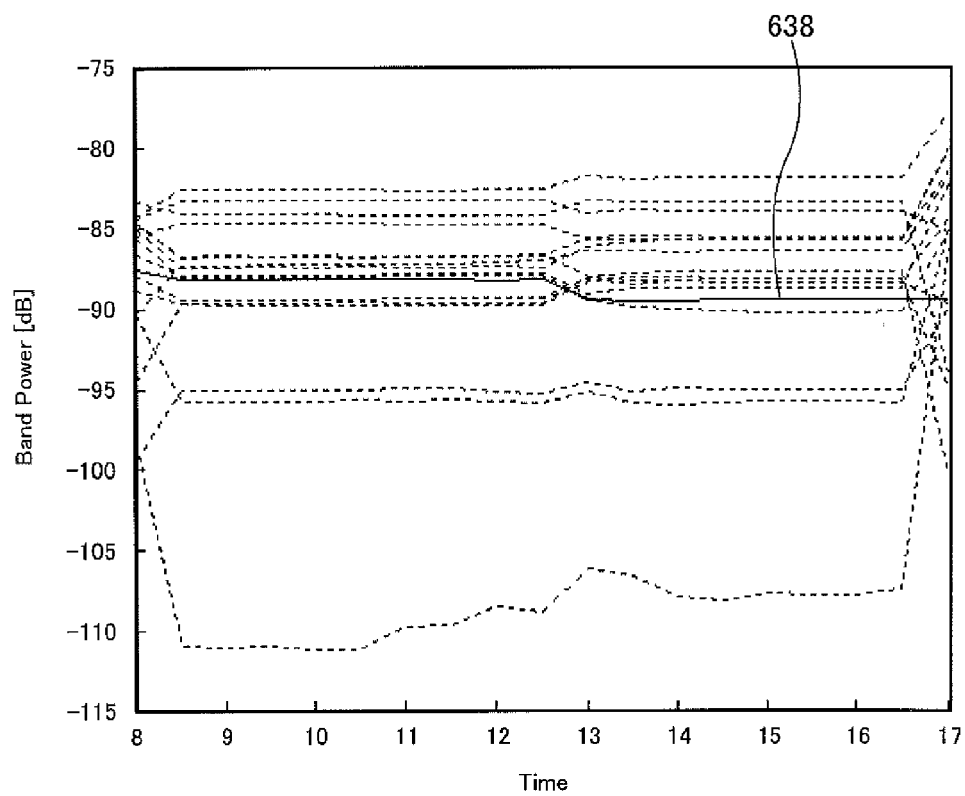
FIG. 18 is a second diagram indicating a state of noise components for a case of pulsed noise that is not coordinated with breathing with respect to Embodiment 2.

FIG. 17 is a diagram showing, through different shades of darkness, the power of each frequency band of the noise components with respect to the same acoustic signal as that in FIG. 15, and is a diagram corresponding to FIG. 15. Furthermore, FIG. 18 is a diagram whose vertical axis represents the power of each frequency band in FIG. 17, and is a diagram corresponding to FIG. 16.

As shown in FIG. 17, when a lot of noise components not synchronized with the breathing sounds are included in the acoustic signal, power becomes high at frequency bands other than frequency band 637, which is in the vicinity of approximately 0.2 Hz, which corresponds to the breathing cycle. Accordingly, the power of frequency band 637 in FIG. 17 as indicated by solid line 638 in FIG. 18 does not rank high with respect to the vertical axis representing the power of the frequency band.

Accordingly, through its determination as to whether or not the breathing sound peak frequency band (in this case corresponding to solid line 634) ranks high in the noise power ranking, bioacoustic processing apparatus 300*a* is able to accurately determine whether or not the occurrences of noise components are in sync with breathing.

Thus, bioacoustic processing apparatus 300*a* according to the present embodiment is able to classify noise components of an acoustic signal into a plurality of noise types respectively corresponding to different attachment states of bioacoustic sensor 200*a*.

Thus, bioacoustic processing apparatus 300*a* becomes able to prompt the user to improve the attachment state of bioacoustic sensor 200*a*, thereby mitigating drops in analytical accuracy for body sounds resulting from the attachment state of bioacoustic sensor 200*a*. Furthermore, bioacoustic processing apparatus 300*a* is able to prevent the same attachment state that causes noise from being repeated.

Furthermore, based on the rate of change in the power of the noise components, bioacoustic processing apparatus 300*a* is able to classify the noise components into a plurality of noise types respectively corresponding to different attachment states of lead wire 220*a*.

Thus, when there is a possibility that the noise components stem from the attachment state of lead wire 220*a*, bioacoustic processing apparatus 300*a* could suggest to the user that lead wire 220*a* be re-stuck. In other words, by being able to actively suggest a task that is relatively simple, bioacoustic processing apparatus 300*a* is able to increase the rate at which the attachment state of the bioacoustic sensor is improved, and to reliably mitigate the above-mentioned drops in analytical accuracy.

Furthermore, based on the synchronization between the noise components and breathing sound components in the acoustic signal, bioacoustic processing apparatus 300*a* classifies the noise components into a plurality of noise types respectively corresponding to different attachment states of adhesive surface 230*a* of bioacoustic sensor 200*a*.

Thus, when there is a possibility that the noise components stem from the attachment state of adhesive surface 230*a*, bioacoustic processing apparatus 300*a* could suggest to the user that adhesive surface 230*a* be re-stuck.

Furthermore, bioacoustic processing apparatus 300*a* extracts breathing sound components from an acoustic signal.

Thus, even if there are personal differences in breathing cycle, or variations due to time, bioacoustic processing apparatus 300*a* is able to accurately classify noise components, and take appropriate measures for noise improvement. In other words, bioacoustic processing apparatus 300*a* is able to mitigate the above-mentioned drops in analytical accuracy more reliably.

Furthermore, bioacoustic processing apparatus 300*a* is able to appropriately give noise countermeasure instructions to the user.

Thus, bioacoustic processing apparatus 300*a* is able to prevent situations where adhesive surface 230*a* would get re-stuck over and over even though the cause lies with lead wire 220*a*, for example. In other words, bioacoustic processing apparatus 300*a* is able to offer appropriate noise countermeasure guidance that narrows down the cause of noise. Accordingly, bioacoustic processing apparatus 300*a* is able to provide a clean acoustic signal with limited noise components, while steering the user clear of unnecessary tasks.

Although, for Embodiment 2, a bioacoustic processing apparatus according to the claimed invention has been described on the assumption that it processes an acoustic signal of a bioacoustic sensor having a lead wire, this is by no means limiting. A bioacoustic processing apparatus may also process an acoustic signal of a wireless bioacoustic sensor, as mentioned above. In this case, the noise type-countermeasure correspondence table would not have to include noise countermeasures corresponding to lead wire states.

Furthermore, a noise type classification section of Embodiment 2 may also perform classification, through processing in the time-domain, in terms of the rate of change in the power of the noise components. By way of example, the noise type classification section may perform classification based on the rate of power change of the noise components, taking those that change fast to be pulsed noise, and those that change slowly to be frictional noise.

Specifically, a change rate/synchronization determination section may measure the period over which a state where the power of the noise components exceeds a predetermined threshold continues, for example. Then, if the duration thereof exceeds 100 msec, the change rate/synchronization determination section determines that the noise components of the acoustic signal are frictional in nature. On the other hand, if the duration thereof does not exceed 100 msec, the change rate/synchronization determination section determines that the noise components of the acoustic signal are of a pulsed nature.

Furthermore, if the bioacoustic processing apparatus is capable of appropriately processing acoustic signals in accordance with each noise type stemming from the attachment state of the bioacoustic sensor, the noise type classification result may be reflected in noise signal processing instead of in the noise countermeasure guidance. Alternatively, the bioacoustic processing apparatus may reflect the noise type classification result in noise signal processing along with the noise countermeasure guidance. In this case, the noise signal processing section stores a signal processing method for each noise type, and applies the signal processing method corresponding to the noise classification result, for example. In this case, too, the bioacoustic processing apparatus is able to mitigate drops in analytical accuracy for body sounds resulting from the attachment state of the bioacoustic sensor.

Although, for Embodiment 2, the claimed invention is applied to a bioacoustic processing apparatus that measures a human's heart sounds or breathing sounds (lung sounds) as body sounds, this is by no means limiting. The claimed invention may be applied to an apparatus that measures other body sounds detectable from a body surface, or body sounds of animals.

A bioacoustic processing apparatus according to the claimed invention may be disposed inside an apparatus that analyzes acoustic signals (e.g., a lung sound diagnostic apparatus, a heart sound diagnostic apparatus, and/or the like) including an information output apparatus, or inside a bioacoustic sensor.

The disclosures of the specifications, drawings, and abstracts included in Japanese Patent Application Nos. 2011-067215 and 2011-067216, both filed on Mar. 25, 2011, are incorporated herein by reference in their entirety.

INDUSTRIAL APPLICABILITY

A bioacoustic processing apparatus and bioacoustic processing method according to the claimed invention are useful as a bioacoustic processing apparatus and bioacoustic processing method that are capable of outputting information indicating the current attachment state of a bioacoustic sensor.

REFERENCE SIGNS LIST

100 Bioacoustic processing system
200, 200a Bioacoustic sensor
210a Main body section
220a Lead wire
230a Adhesive surface
300, 300a Bioacoustic processing apparatus
310a Acoustic signal input section
320, 320a Noise extraction section
330a Breathing sound extraction section
340, 340a Noise type classification section
341a Short-term noise change analysis section
342a Long-term noise change analysis section
343a Long-term breathing sound change analysis section
344a Change rate/synchronization determination section
350a Noise countermeasure guidance section
360a Noise amount determination section
370a Noise countermeasure control section
380a Noise signal processing section
400 Information output apparatus
510 Body surface
520 Double-sided tape
530 Surgical tape

The invention claimed is:

1. A bioacoustic processing apparatus that processes an acoustic signal of a bioacoustic sensor attached to a body surface, the bioacoustic processing apparatus comprising:
   one or more memories; and
   a circuitry operative to:
      extract, from the acoustic signal, a noise component included in the acoustic signal;
      extract, from the acoustic signal, a breathing sound component included in the acoustic signal;
      determine whether or not the extracted noise component is synchronized with the extracted breathing sound component;
      classify the extracted noise component into a first noise type, when the noise component is synchronized with the extracted breathing sound component; and
      classify the extracted noise component into a second noise type being different from the first noise type, when the noise component is unsynchronized with the extracted breathing sound component.

2. The bioacoustic processing apparatus according to claim 1, wherein the circuitry further operative to
   determine whether or not rate of change in power of the extracted noise component is larger than a first predetermined threshold; and
   classify the extracted noise component into third noise type being different from the first noise type and the second noise, when the rate of change in power of the extracted noise component is smaller than or equal to the first predetermined threshold.

3. The bioacoustics processing apparatus according to claim 2,
   wherein
   the extracted noise component is classified into either the first noise type or the second noise type, when the rate of change is larger than the first predetermined threshold.

4. The bioacoustic processing apparatus according to claim 2,
   wherein
   the bioacoustic sensor comprises a lead wire carrying the acoustic signal and an adhesive surface attached to the body surface, and
   the noise component is caused by attachment state of the lead wire or the adhesive surface.

5. The bioacoustic processing apparatus according to claim 4,
   wherein the first noise type corresponds to first attachment state where the tension in the lead wire is high or where the adhesive strength of the adhesive surface is weak, the second noise type corresponds to second attachment state where something is in intermittent contact with the lead wire or where an air bubble is trapped under the adhesive surface, and the third noise type corresponds to third attachment state where something is rubbing against the lead wire.

6. The bioacoustic processing apparatus according to claim 5, wherein the circuitry further operative to determine whether or not amount of the extracted noise component is larger than a second predetermined threshold; and classify the extracted noise component into fourth noise type being different from the first noise type, the second noise type and the third noise type, when the amount of the extracted noise component is smaller than or equal to the second predetermined threshold, wherein the noise component is classified into either the first noise type, the second noise type, or the third noise type, when the extracted noise component is larger than the second predetermined threshold.

7. The bioacoustic processing apparatus according to claim 4, wherein the circuitry further operative to notify to a user information urging an improvement of the attachment state, the information corresponding to the result of the classification.

8. The bioacoustic processing apparatus according to claim 7, wherein the information is notified by at least one of displaying an image and outputting audio.

9. A bioacoustic processing method that processes an acoustic signal of a bioacoustic sensor attached to a body surface, the bioacoustic processing method comprising:

extracting, from the acoustic signal, a noise component included in the acoustic signal;

extracting, from the acoustic signal, a breathing sound component included in the acoustic signal;

determining whether or not rate of change in power of the extracted noise component is larger than a first predetermined threshold;

classifying the extracted noise component into a first noise type, when the noise component is synchronized with the extracted breathing sound component, and the extracted noise component into a second noise type being different from the first noise type, when the noise component is unsynchronized with the extracted breathing sound component; and outputting information corresponding to a result of the classification, wherein at least one of the extracting, the determining, the classifying, and the outputting is performed by a circuitry.

* * * * *